(12) United States Patent
Sartor et al.

(10) Patent No.: US 11,832,935 B2
(45) Date of Patent: Dec. 5, 2023

(54) DEVICE, SYSTEM AND METHOD FOR CALORIC INTAKE DETECTION

(71) Applicant: KONINKLIJKE PHILIPS N.V., Eindhoven (NL)

(72) Inventors: Francesco Sartor, Eindhoven (NL); Gabriele Papini, Eindhoven (NL); Zihan Wang, Eindhoven (NL)

(73) Assignee: VERSUNI HOLDING B.V., Eindhoven (NL)

( * ) Notice: Subject to any disclaimer, the term of this patent is extended or adjusted under 35 U.S.C. 154(b) by 1258 days.

(21) Appl. No.: 16/323,982

(22) PCT Filed: Aug. 14, 2017

(86) PCT No.: PCT/EP2017/070549
§ 371 (c)(1),
(2) Date: Feb. 7, 2019

(87) PCT Pub. No.: WO2018/033504
PCT Pub. Date: Feb. 22, 2018

(65) Prior Publication Data
US 2019/0167154 A1 Jun. 6, 2019

(30) Foreign Application Priority Data
Aug. 18, 2016 (EP) ..................................... 16184732

(51) Int. Cl.
*A61B 5/113* (2006.01)
*A61B 5/00* (2006.01)
(Continued)

(52) U.S. Cl.
CPC ............ *A61B 5/113* (2013.01); *A61B 5/0806* (2013.01); *A61B 5/0816* (2013.01); *A61B 5/11* (2013.01);
(Continued)

(58) Field of Classification Search
None
See application file for complete search history.

(56) References Cited

U.S. PATENT DOCUMENTS

2006/0064037 A1   3/2006   Shalon
2008/0275349 A1*  11/2008  Halperin ................ A61B 5/447
                                                  600/364
(Continued)

FOREIGN PATENT DOCUMENTS

CN   102065754 A   5/2011
CN   102114321 A   7/2011
(Continued)

OTHER PUBLICATIONS

Dong et al, Wearable Sensing for Liquid Intake Monitoring via Apnea Detection in Breathing Signals, 2014, Biomedical Engineering Letters, The Korean Society of Medical and Biological Engineering, Korea, vol. 4, No. 4, pp. 378-387 (Year: 2014).*

(Continued)

*Primary Examiner* — Michael R Bloch
(74) *Attorney, Agent, or Firm* — Maschoff Brennan

(57) ABSTRACT

The present invention relates to a device, system and method for automatic and unobtrusive caloric intake detection. The device comprises a respiration input for obtaining a respiration signal indicating the subject's respiration, and an analysis unit for analyzing the obtained respiration signal in the frequency domain by determining one or more respiration signal features from the obtained respiration signal in the frequency domain related to changes in oxidation and by (Continued)

detecting changes of the one or more determined respiration signal features to detect periods of caloric intake by the subject.

14 Claims, 5 Drawing Sheets

(51) Int. Cl.
*A61B 5/08* (2006.01)
*A61B 5/11* (2006.01)

(52) U.S. Cl.
CPC .......... *A61B 5/1118* (2013.01); *A61B 5/4866* (2013.01); *A61B 5/6831* (2013.01); *A61B 5/721* (2013.01); *A61B 5/7267* (2013.01); *A61B 5/1135* (2013.01); *A61B 5/6824* (2013.01)

(56) References Cited

U.S. PATENT DOCUMENTS

| | | | |
|---|---|---|---|
| 2011/0152636 A1 | 6/2011 | Jang | |
| 2014/0163343 A1 | 6/2014 | Heneghan | |
| 2015/0080672 A1* | 3/2015 | Biswas | A61B 5/1135 600/301 |
| 2015/0148625 A1 | 5/2015 | Benaron | |
| 2016/0012749 A1* | 1/2016 | Connor | A61B 5/24 600/27 |

FOREIGN PATENT DOCUMENTS

| | | |
|---|---|---|
| FR | 2940038 A1 | 6/2010 |
| WO | 2008157622 A1 | 12/2008 |
| WO | 2016038585 A1 | 3/2016 |

OTHER PUBLICATIONS

Dong Bo et al: "Wearable sensing for liquid intake monitoring via apnea detection in breathing signals", Biomedical Engineering Letters, The Korean Society of Medical and Biological Engineering, Korea, vol. 4, No. 4, Oct. 11, 2014 (Oct. 11, 2014), pp. 378-387.

John Smith et al: "Coordination of Eating, Drinking and Breathing in Adults", Chest, vol. 96, No. 3, Sep. 1, 1989 (Sep. 1, 1989), pp. 578-582.

Karen M. Hiiemae et al: "Eating and Breathing: Interactions Between Respiration and Feeding on Solid Food", Dysphagia, vol. 18, No. 3, Aug. 1, 2003 (Aug. 1, 2003), pp. 169-178.

Özyener, F., Rossiter, H. B., Ward, S. A. and Whipp, B. J. (2001), Influence of exercise intensity on the on- and off-transient kinetics of pulmonary oxygen uptake in humans. The Journal of Physiology, 533: 891-902.

Dong Bo et al: Wearable diet monitoring through breathing signal analysis:, The Effect of Applied Compressive Loading on Tissue-Engineered Cartilage Contructs Cultured With TGF-BETA3, IEEE, Jul. 3, 2013, pp. 1186-1189.

* cited by examiner

DEVICE, SYSTEM AND METHOD FOR CALORIC INTAKE DETECTION

This application is the U.S. National Phase application under 35 U.S.C. § 371 of International Application No. PCT/EP2017/070549, filed on Aug. 14, 2017, which claims the benefit of International Application No. 16184732.2 filed on Aug. 18, 2016. These applications are hereby incorporated by reference herein.

FIELD OF THE INVENTION

The present invention relates to a device, system and method for caloric intake detection.

BACKGROUND OF THE INVENTION

Caloric intake (i.e. food/drink intake) is a crucial piece of information in any lifestyle coaching service. It can have clinical application, such as malnutrition, overnutrition, as well as sports applications in supplementation or optimal meal timing. Food intake reporting is also a problem area in the field of elderly care. Additionally, it is relevant for new-born nutrition and some patients categories such as cancer patients, where malnutrition is a primary determinant of low survival. However, it is at the moment not assessable via an unobtrusive effortless method. Users are asked to indicate when they ingest anything and often to detail what they ingest. This is a cumbersome and time-consuming procedure which suffers of underreporting and poor adherence.

US 2015/080672 A1 discloses a wearable breathing sensor, such as a piezoelectric chest belt system, for generating a breathing signal that is analyzed by a classifier to identify apnea patterns indicating that the subject has swallowed during breathing. These breathing signals are computer-analyzed to extract inferences regarding the subject's eating and drinking patterns and thereby provide data for monitoring food or beverage intake for remote health monitoring.

DONG B O ET AL: "Wearable sensing for liquid intake monitoring via apnea detection in breathing signals", BIOMEDICAL ENGINEERING LETTERS, THE KOREAN SOCIETY OF MEDICAL AND BIOLOGICAL ENGINEERING, KOREA, vol. 4, no. 4, 11 Oct. 2014, pages 378-387, describes a system that works based on the observation that a person's otherwise continuous breathing process is interrupted by a short apnea when a swallow occurs as a part of the intake process and that detects the swallows via recognizing apneas extracted from breathing signal captured by a wearable sensor chest-belt.

JOHN SMITH ET AL: "Coordination of Eating, Drinking and Breathing in Adults", CHEST, vol. 96, no. 3, 1 Sep. 1989, pages 578-582, describes a study of the coordination of breathing and swallowing at rest as well as during eating and drinking Ventilation was monitored using respiratory inductive plethysmography and swallowing was recorded by submental electromyogram.

KAREN M. HIIEMAE ET AL: "Eating and Breathing: Interactions Between Respiration and Feeding on Solid Food", DYSPHAGIA, vol. 18, no. 3, 1 Aug. 2003, pages 169-178, describes a study to determine how eating, especially bolus formation in the pharynx, affects respiration. Nasal air pressures, masseter electromyography (EMG), and videofluorography (VFG) were examined.

SUMMARY OF THE INVENTION

It is an object of the present invention to provide to a device, system and method for a more accurate and unobtrusive caloric intake detection.

In a first aspect of the present invention a device for caloric intake detection is presented comprising
  a respiration input for obtaining a respiration signal indicating the subject's respiration,
  an analysis unit for analyzing the obtained respiration signal in the frequency domain by determining one or more respiration signal features from the obtained respiration signal in the frequency domain related to changes in oxidation and by detecting changes of the one or more determined respiration signal features to detect periods of caloric intake by the subject.

In a further aspect of the present invention a system for caloric intake detection is presented comprising
  a respiration sensor for detecting a subject's respiration and for generating a respiration signal indicating the subject's respiration, and
  a device for caloric intake detection based on the generated respiration signal.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea that more oxygen is needed when the caloric content of foods and/or drinks (i.e. regardless if solid or fluid) is broken down and oxidized to provide energy. Consequently, the living being breathes deeper (leading to increased amplitude) and/or faster (leading to increased frequency/decreased inter-breath intervals), which eventually determines an alteration in respiratory rate variability. This idea is exploited by the present invention to detect when caloric intake occurs by evaluating respiration signal features (in the frequency domain), in particular changes of such respiration signal features, which are related to changes in oxidation. The commonly used user-dependent subjective food/drink intake self-report is thus replaced by an automatic unobtrusive approach based on respiration signal features, e.g. respiration patterns.

In this context respiration signal features shall be understood as a statistically or, more generally, a mathematically derived parameter, which describes a typical behavior present in the signal. Examples of respiration signal features are: the dominant frequency, the amplitude of the signal corresponding to the dominant frequency, mean distance between the breaths, the variance of the distances between the breaths, etc.

Contrary to the above-cited US 2015/080672 A1, the present invention does not require detecting swallowing events. Additionally, detecting swallowing would be confused by artifacts such as talking, coughing, etc. According to the present invention, these types of artifacts are filtered out. Different from US 2015/080672 A1, the present invention looks into stable breathing patterns, which are representing how respiration is characterized over a certain period of time. This is an advantage compared to swallowing detection since the latter would always require high quality respiration waves in order to catheterize the morphology of the signal. According to the present invention the high accuracy morphology is not needed, even though it could optionally be used. Known methods look at swallowing and/or apnea events associated with caloric intake. The limitation of these methods is the lack of a link with actual energy absorption. For instance, a subject could swallow water, or saliva or mucus, which would then be counted as caloric intake according to such known methods, whereas this would not be counted as caloric intake according to the present invention.

According to the present invention respiration signal features are obtained from the respiration signal in the frequency domain, i.e. from a representation of the respiration signal in the frequency domain. Generally all possible feature domains of the respiration signal features may be evaluated, i.e. features in time and frequency as well as non-linear features and combinations of features. Preferably, said analysis unit is configured to determine one or more of the frequency spectrum, the dominant frequency, the inter-breath interval length and amplitude of the respiration signal as one or more respiration signal features. These features generally show significant changes when comparing them before, during and after caloric intake and thus lead to a good accuracy of caloric intake detection.

In another embodiment said analysis unit is configured to use one or more feature thresholds for detecting changes of the one or more determined respiration signal features. Thus, one of more features values may be compared with thresholds to detect changes. The features thresholds may be determined in advance, e.g. through measurements or simulations. Feature thresholds may be defined in general for all subjects, or may be assigned to groups of subjects (e.g. according to criteria like weight, age, gender, health condition, etc.), or may even defined individually for a monitored subject (e.g. after a training phase of the system).

In a further embodiment said analysis unit is configured to select subsequent time windows, in particular overlapping time windows, of the obtained respiration signal for the analysis by the analysis unit and to detect changes of the one or more determined respiration signal features among selected subsequent time windows. In this way, changes of one or more respiration signal feature from one time window to the next time window are comparable in a better way.

Hereby, the device may further comprise an activity input for obtaining activity data indicating a subject's physical activity and said analysis unit may be configured to select time windows for the analysis based on the activity data. Since activity may distort or tamper the respiration signal and the detection of respiration signal features, the activity data will help to select appropriate time windows in which the respiration signal is not distorted or tampered by subject activity (such as walking around or running)

The analysis unit is thus preferably configured to select time windows in which the activity data indicate no activity or an activity related to caloric food intake or an activity below a predetermined intensity. For instance, if the subject is sitting still or is only slowly moving the upper part of the body while sitting and eating, the activity data will indicate no or only low-level activity so that time windows of the respiration signal during such periods can be used for the analysis, while time windows during which the subject walks around in the room while eating will be excluded from the analysis.

The analysis unit may also be configured to determine the duration of the time windows based on the intensity and duration of a detected activity. By use of the physical activity, e.g. through a physical activity classifier, unreliable elevated respiration values non linkable to caloric intake can be removed. Moreover, intensity and duration of the activity may be used to determine the level of hyperventilation (elevated respiration) and recovery time. Based on this information the duration of the time windows may be selected appropriately. Still further, respiration waves, which may be distorted by coughing or speaking, may be removed.

In another embodiment the analysis unit is configured to detect pre-prandial and post-prandial periods based on the detected changes of the one or more determined respiration signal features. Particularly the changes in respiratory features are detected as caloric intake, which means that it is distinguished between pre-prandial (or fasting) and post-prandial (or fed) periods.

Further, the analysis unit may be configured to determine the inter-breath interval length as one respiration signal feature and to detect a post-prandial period if the inter-breath interval length decreases. In another embodiment the dominant frequency may be used additionally or alternatively, i.e. said analysis unit may be configured to determine the dominant frequency as one respiration signal feature and to detect a post-prandial period if the dominant frequency increases.

Generally, any kind of sensor that is able to provide a respiration signal may be used. Preferably, the respiration sensor comprises a wearable sensor, in particular a respiration belt, a wrist worn sensor, an ECG sensor, or a contact photoplethysmography sensor, or a remote sensor, in particular a remote photoplethysmography sensor or a camera. Thus, the respiration signal can be acquired by a contact or non-contact (remote) sensor.

The system may further comprise an activity sensor, in particular an accelerometer or a remote camera, for acquiring activity data indicating a subject's physical activity. Both the activity sensor and the respiration sensor may be integrated into a common user device worn by the subject. For instance, the user device may be a smartphone, wrist watch, etc., wherein appropriate sensors are additionally provided or existing sensors (e.g. the inertial sensor as commonly provided in a smartphone) may be used to acquire a respiration signal and/or activity data.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
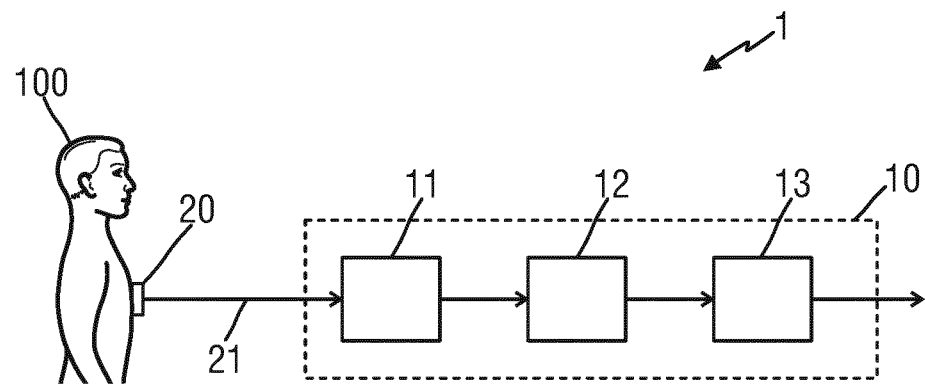
FIG. 1 shows a schematic diagram of a first embodiment of a system and a device according to the present invention.

FIG. 1 shows a schematic diagram of a first embodiment of a system 1 and a device 10 for caloric intake detection of a subject 100 according to the present invention.

The system 1 comprises a respiration sensor 20 for detecting a subject's respiration and for generating a respiration signal 21 indicating the subject's respiration. In this embodiment the respiration sensor 20 is a wearable sensor that is worn at the subject's body, in this example a respiration belt (e.g. band holding a piezo element as sensor to monitor movements of the chest reflecting the subject's respiration). Other usable wearable sensors include a wrist worn sensor, an ECG sensor, or a contact photoplethysmography sensor.

The system 1 further comprises a device 10 for caloric intake detection based on the generated respiration signal 21.

The device 10 includes a respiration input 11 for obtaining (i.e. receiving or retrieving the respiration signal 21 indicating the subject's respiration as acquired by the respiration sensor 20. For the communication of the respiration signal 21 to the device 10 generally any possible way of communication may be used. For instance, the respiration sensor 20 may be connected to the device 10 through wires (e.g. directly or via a computer network, such as a LAN) or in a wireless manner, e.g. a communication network (e.g. UMTS, LTE, etc.) or another wireless network (e.g. WiFi, Bluetooth, Zigbee, etc.). The respiration input 11 may thus e.g. be a corresponding data interface, such as a Bluetooth interface, a WiFi interface, a wired terminal, etc.

The device 10 further comprises an analysis unit 12 for analyzing the obtained respiration signal 21 by determining one or more respiration signal features and detecting changes of the one or more determined respiration signal features to detect periods of caloric intake by the subject. This will be explained in more detail below, for instance with reference to FIGS. 3 to 5. The analysis unit 12 may e.g. be implemented in hard- and/or software, as one or more programmed processors or computers (e.g. a hospital workstation, a caregiver's PC, etc.) or as an application running on a user device (e.g. a smartphone, laptop, tablet, etc.).

The device 10 may further comprise an output 13 for issuing a caloric intake information that indicates detected information about the subject's caloric intake, such as the number and periods of intake within a certain time frame (e.g. during a whole day) or eating behaviors (e.g. eating frequency). The output 13 may e.g. an output interface for communicating the caloric intake information, to a remote destination, e.g. a nurse's user device, a central supervision monitor, etc., or may be a user interface, like a display and/or loudspeaker, that directly issues (visible and/or audible) the caloric intake information, e.g. as a table or diagram. In a particular application scenario an alarm notice may be issued if it is found that the caloric intake, e.g. of an elderly person or a patient, was much too low over a certain period so that e.g. a caregiver is notified to take care of this situation.

Figure 2:
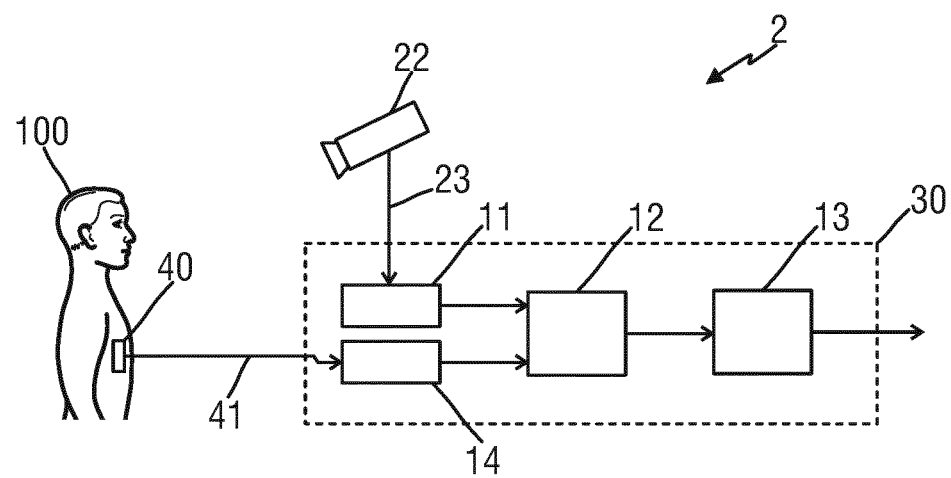
FIG. 2 shows a schematic diagram of a second embodiment of a system and a device according to the present invention.

FIG. 2 shows a schematic diagram of a second embodiment of a system 2 and a device 30 according to the present invention. In this embodiment the system 2 comprises a remote sensor 22 as respiration sensor, in particular a camera for acquiring video data of the subject 100. From the movements of the chest or belly area extracted from the video data in a commonly known way (e.g. by image processing methods) a respiration signal 23 can be derived that is provided to the respiration input 11 of the device 30.

Additionally, the system 2 comprises an activity sensor 40, in this example an accelerometer mounted to the subject's upper body (e.g. by a chest belt) for acquiring activity data 41 indicating a subject's physical activity. In other embodiments, the activity sensor 40 may be mounted to other body portions, e.g. an arm, a leg, etc., or may be of a different type. For instance the video data 23 acquired by the camera 22 may also be used as activity data to detect physical activity of the subject 100.

The device 30 comprises an activity input 14 for obtaining (i.e. receiving or retrieving) the activity data 41. Generally, the same options exist for implementation of the activity input 41 and the way of communicating the activity data that have been explained above for the respiration input 11 and the respiration data 21. The analysis unit 12 is configured to select time windows for the analysis based on the activity data 41, i.e. to select portion of the respiration signal 21 at which the subject's activity does not or not substantially distort or tamper the respiration signal 21. This improves the accuracy of the caloric intake detection.

Thus, according to an embodiment of the present invention a continuous unobtrusive respiration signal may be used, which can be collected by means of one or more unobtrusive wearable (s) (e.g. of a piezo respiration band, PPG watch) as well as one or more contactless sensor(s) (e.g. vital signs camera) is used here to quantify the oxygen need of a living being which is correlated with the caloric intake of the living being.

According to the present invention respiration is generally seen as a periodic wave signal. Known methods need to identify an interruption of the periodicity, generated for example by an apnea due to ingestion (in the time domain). Known methods are limited by the fact that apneas can be generated by several other behaviors. The present invention looks instead at the frequency domain, following the principle that caloric intake produced increases oxygen need. The consequent increases in $O_2$ intake is mainly achieved by a combination of changes in respiration frequency (faster), amplitude (greater), and variability in general (variability takes into account both frequency and amplitude changes). It is noted that higher $O_2$ demand is also induced by exercise, which is the reason why it is preferred in an embodiment to detect these episodes and understand when full recovery has been achieved.

Figure 3:
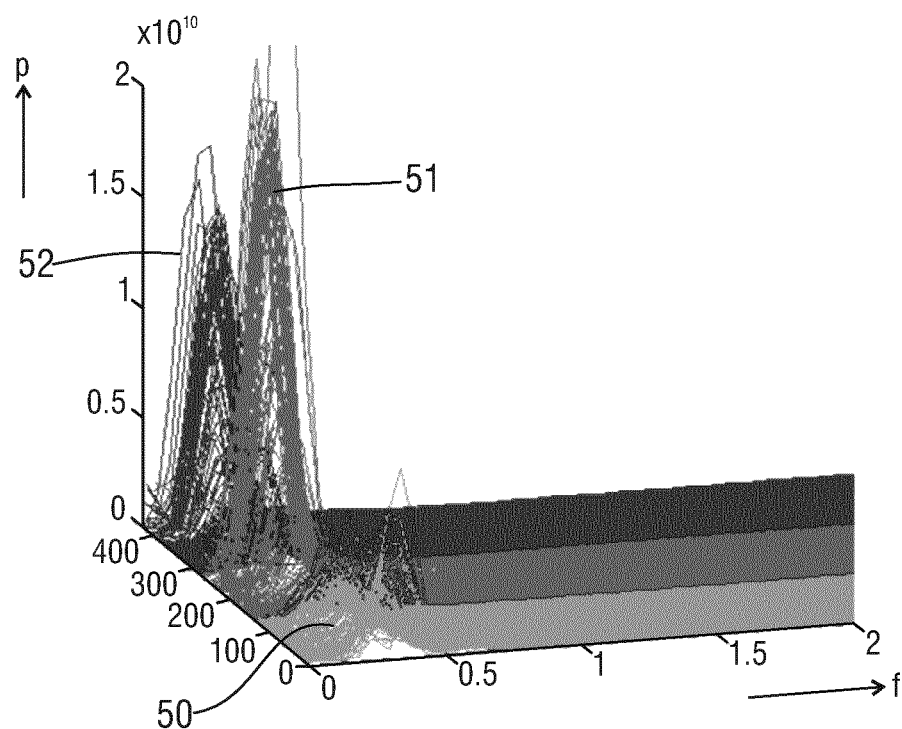
FIG. 3 shows a diagram illustrating a running spectral analysis of a subject in a pre-prandial and post-prandial phase.

Thus, only caloric intake can increase oxidation, because the body has to burn the food/drinks ingested or expend oxygen to build new protein. Non-caloric intake does not affect oxidation. In fact, this is a clear advantage over known approaches, which cannot recognize the difference between swallowing saliva, water, etc. from caloric intake by consumption of food and/or drinks FIG. 3 shows a diagram illustrating a running spectral analysis of a respiration signal of a single subject in a pre-prandial and post-prandial phase. The diagram shows the power amplitude P over the frequency fat different moments in time. It can be appreciated in this diagram how the respiration spectral signal can differ from before having consumed a meal (curves 50) to immediately after (curves 51) and again to 3 hours after the meal (curves 52). These data were acquired with a piezo respiration band. This figure thus clearly proofs that the eating period can be identified.

Looking at the y-axis (time) the difference in signal amplitude between the peak (in curve 51) and the preceding interval (curve 50) is clearly visible. By comparing these two segments it can be determined that caloric intake happened in the time frame between the time at which the respiration signal represented by curve 50 and the time at which the respiration signal represented by curve 51 have been acquired.

Examples of respiration signal features, which detect intake, are dominant frequency and respiration variability, in this case inter-breath intervals. However, more respiration-derived features in the time and frequency as well as non-linear domains as well as combinations thereof can be used.

The present invention generally works at rest and preferably looks into stable breathing patterns. In this context, a "stable breathing pattern" means respiration that is far enough from significant physical activity moments which would alter the metabolic rate. The level of physical activity and the duration of its effect on the metabolic rate and the respiration can e.g. be easily modeled by using a motion sensor (e.g. accelerometer). When motion is above a given threshold the analysis of the respiration signal applied according to the present will not take the input into account. When the motion is below a certain threshold, given the motion history in terms of bout intensity and duration (which determine the time constant), the analysis will be kept on hold until the time constant determines that the effect of the activity bout over the metabolic rate and respiration is ceased. How to model how to assess this time constant is generally known, e.g. from Ozyener, F., Rossiter, H. B., Ward, S. A. and Whipp, B. J. (2001), Influence of exercise intensity on the on- and off-transient kinetics of pulmonary oxygen uptake in humans. The Journal of Physiology, 533: 891-902.

Figure 4:
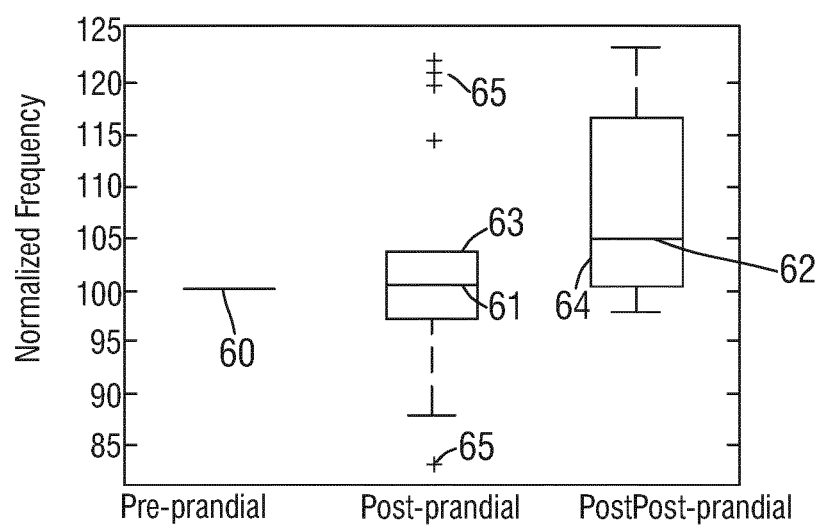
FIG. 4 shows a diagram illustrating the dominant frequency of a respiration signal of a subject in a pre-prandial and post-prandial phase.

FIG. 4 shows a diagram illustrating the dominant frequency of a respiration signal of a subject in a pre-prandial and post-prandial phase. FIG. 4 particularly shows how the dominant frequency increases with digestion. These data are based on 10 subjects who had different meals ranging from 300 kcal to 900 kcal. Results are normalized for pre-meal values. The horizontal lines 60, 61, 62 represent the median values of the dominant frequency distributions, the boxes 63, 64 represent the standard deviations and the crosses 65 represent the outliers. As can be seen, the dominant frequency significantly increases after the meal.

Figure 5:
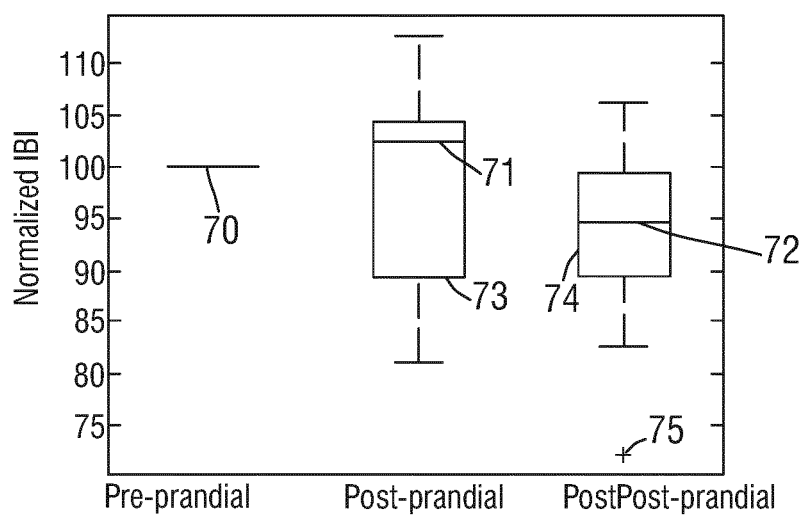
FIG. 5 shows a diagram illustrating the inter-breath interval of a subject in a pre-prandial and post-prandial phase.

FIG. 5 shows a diagram illustrating the inter-breath interval of a subject in a pre-prandial and post-prandial phase. FIG. 5 particularly shows how the inter-breath interval (IBI) decreases with digestion. These data are based on the same 10 subjects who had different meals ranging from 300 kcal to 900 kcal. Results are normalized for pre-meal values. The horizontal lines 70, 71, 72 represent the median values of the IBI distributions, the boxes 73, 74 represent the standard deviations and the cross 75 represents an outlier. As can be seen, the IBI significantly decreases after the meal.

The digestive process starts in the mouth at the time when food and/or drinks are ingested. Caloric intake triggers an increase in the oxidative processes, which as a consequence increases oxygen uptake. According to the present invention it is exploited by analyzing respiration signal features in the frequency domain, in particular changes of the respiration signal in the frequency domain that are related to an increase in oxidation allowing the conclusion that caloric intake of the subject started by ingesting food and/or drinks. This can particularly be determined from time course variations of respiration signal features in the frequency domain, i.e. by monitoring the respiration signal in the frequency domain over time.

Figure 6:
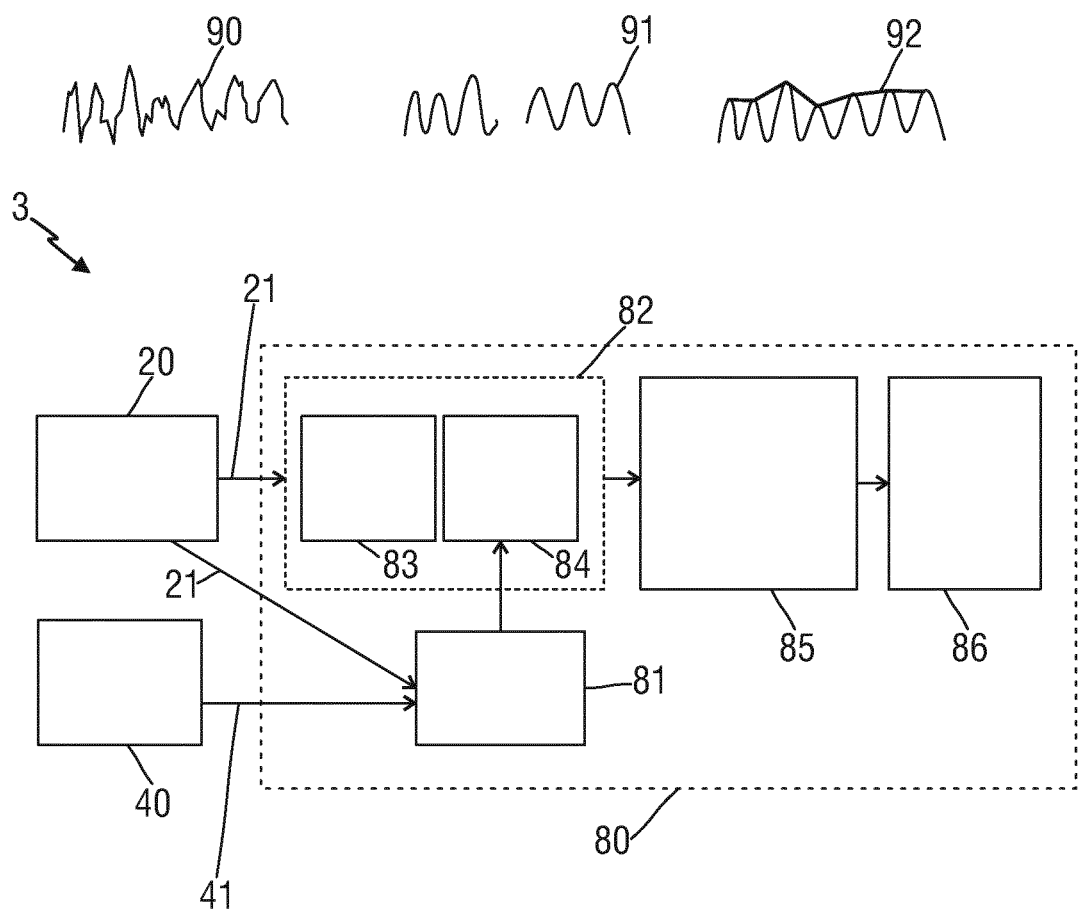
FIG. 6 shows a schematic diagram of a third embodiment of a system and a device according to the present invention and corresponding signals.

FIG. 6 shows a schematic diagram of a third embodiment of a system 3 and a device 80 according to the present invention and corresponding signals. The respiration input 11 and the activity input 14 (as shown in FIG. 2) are omitted in this diagram, but the device 80 only shows the elements of the analysis unit 12 as provided in this embodiment.

The activity classifier 81 classifies if the change in the IBI is due to a previously done physical activity, as retrieved from the activity data 41, allowing the exclusion of the subsequent time window of the respiration signal 21 from the analysis process. The size of the time window is chosen according to the intensity and duration of the physical activity done. The activity classifier 81 allows also selecting segments of the respiration signal 21 when it is stable (e.g. subject is not moving, for instance during sitting activities).

The raw respiration signal 90 may undergo cleaning processing in a cleaning signal processing unit 82, which may include a filter 83 and a concealing unit 84 for filtering and concealing it to obtained a cleaned respiration signal 91. In a feature extraction unit 85 one or more respiration signal features 92 are extracted from the cleaned respiration signal 91. Finally, a classifier 86 is provided for classification into food intake or no food intake in a certain time window.

The cleaning of the signal will be explained below in more detail with reference to FIG. 7. According to this cleaning step stable features will be allocated as follows:
 i) It starts from a raw respiration signal x min long, long enough to assess respiration signal features, time, frequency and nonlinear;
 ii) The signal is segmented in segments long enough to contain at least 3 respiration waves, and overlap windows are used to allow removal of eventual noise.
 iii) Each segment is checked for stability (here combined with step 2 is where things like, talking and coughing are omitted). Stability can be checked for example by looking at the standard deviation of the signal.
 iv) When a minimum number of stable data (for example 50% of the total signal) are obtained, features are calculated.
 v) Values of the features calculated are memorized and these steps are repeated in loops.

There may be a separate element to conceal respiration signal when this is influenced by physical activity about a certain threshold.

In a subsequent process that will be explained below in more detail with reference to FIG. 8 the following steps are taken:
 i) Features are collected at different times: e.g. time 1 and time 2.
 ii) It is checked if features at time 1 and time 2 differ.
 iii) If they do not differ, it is started over with the comparison between other two data points.
 iv) If they differ, the caloric intake is detected.
 v) If the adjacent times are still the same group, then it is avoided to classify the same intake as different intake.

A simple embodiment for the classifier 86 is a threshold driven detection: when the respiration signal feature is above a certain threshold (absolute or depending from the previous period not influenced by food intake or physical activity) the current analyzed time window is classified as subsequent a food intake event. In another embodiment the classifier 86 is implemented using a machine learning technique (e.g. a support vector machine) that can detect the food intake events from more than one respiration signal feature.

In another embodiment the activity classifier 81 can help to quantify the amount of respiration signal due to the activity and filter/remove it without discharge of part of the recordings.

The feasibility of the proposed invention during free-living has been examined. Because part of the respiration signal (segments) are optionally concealed when respiration cannot be detected, is influenced by talking, is influenced by exercise, and/or is affected by artefacts, it has been analyzed what would be the minimum amount of time needed to make accurate estimation of caloric intake events, in particular of eating events. In a random and ascending order segments have been removed to appreciate the minimum time needed to detect a difference when there is a difference between phases. 1000 simulations per observation have been run in order to be able to generalize the results and found that 210 seconds is sufficient to detect an eating event. This 210 s includes a good segment before eating and after eating. Since it can be seen that respiration signal features are altered still 3 hours after a meal 3.5 min of clean data is a feasible target.

Time duration [s] left after concealing segments (1000 simulations per subject) that still allows a caloric intake detection

| | Median Dominant Frequency ± standard deviation |
|---|---|
| Subject 1 | 90 ± 174 |
| Subject 2 | 370 ± 256 |
| Subject 3 | 580 ± 266 |
| Subject 4 | 840 ± 273 |
| Subject 5 | 90 ± 135 |
| Subject 6 | 40 ± 69 |
| Subject 7 | 40 ± 70 |
| Subject 8 | 210 ± 180 |
| Subject 9 | 300 ± 225 |
| Subject 10 | 1010 ± 288 |
| Subject 11 | 30 ± 118 |
| Median | 210 ± 180 |

Figure 7:
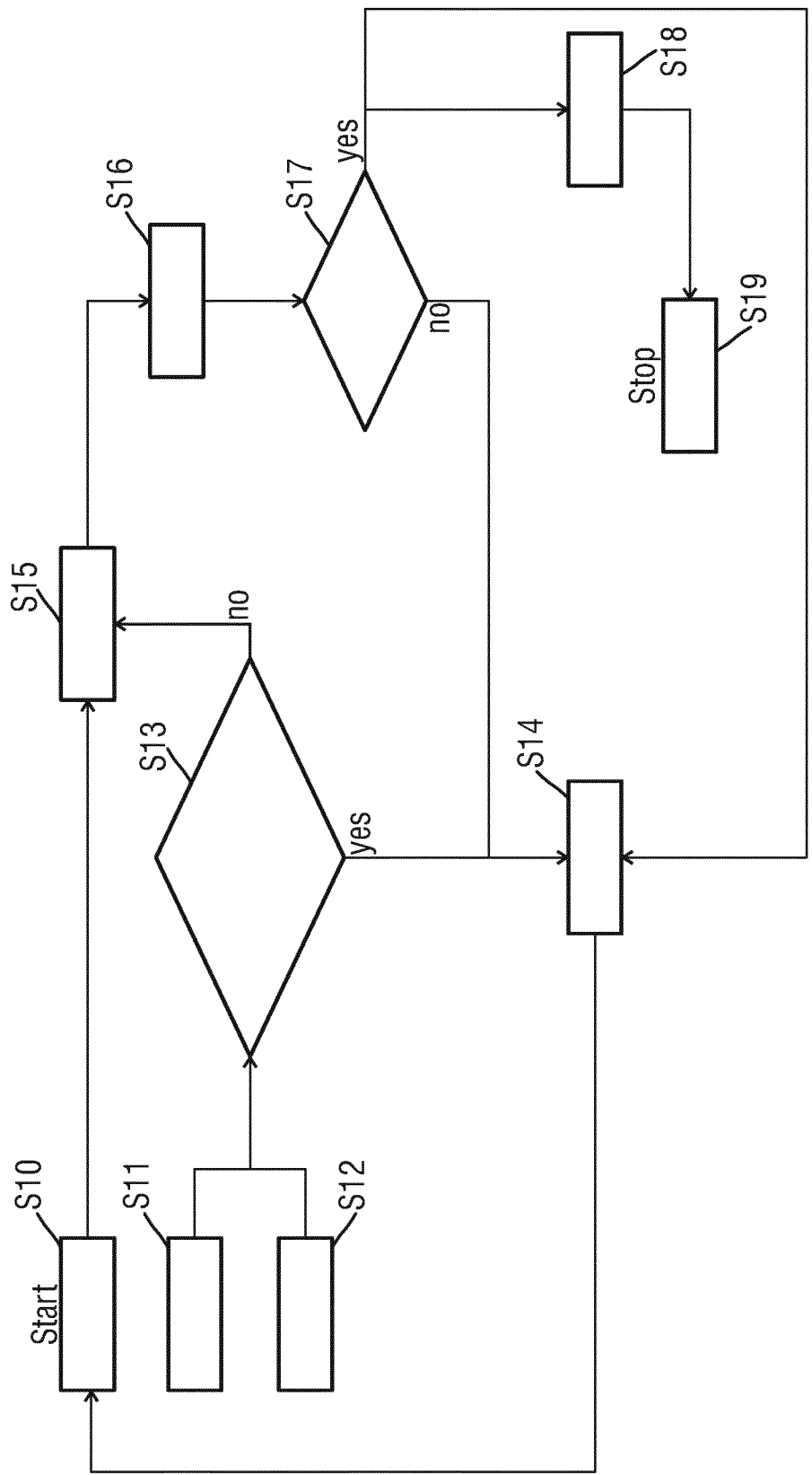
FIG. 7 shows a flow chart of a first part of an embodiment of a method according to the present invention.
Figure 8:
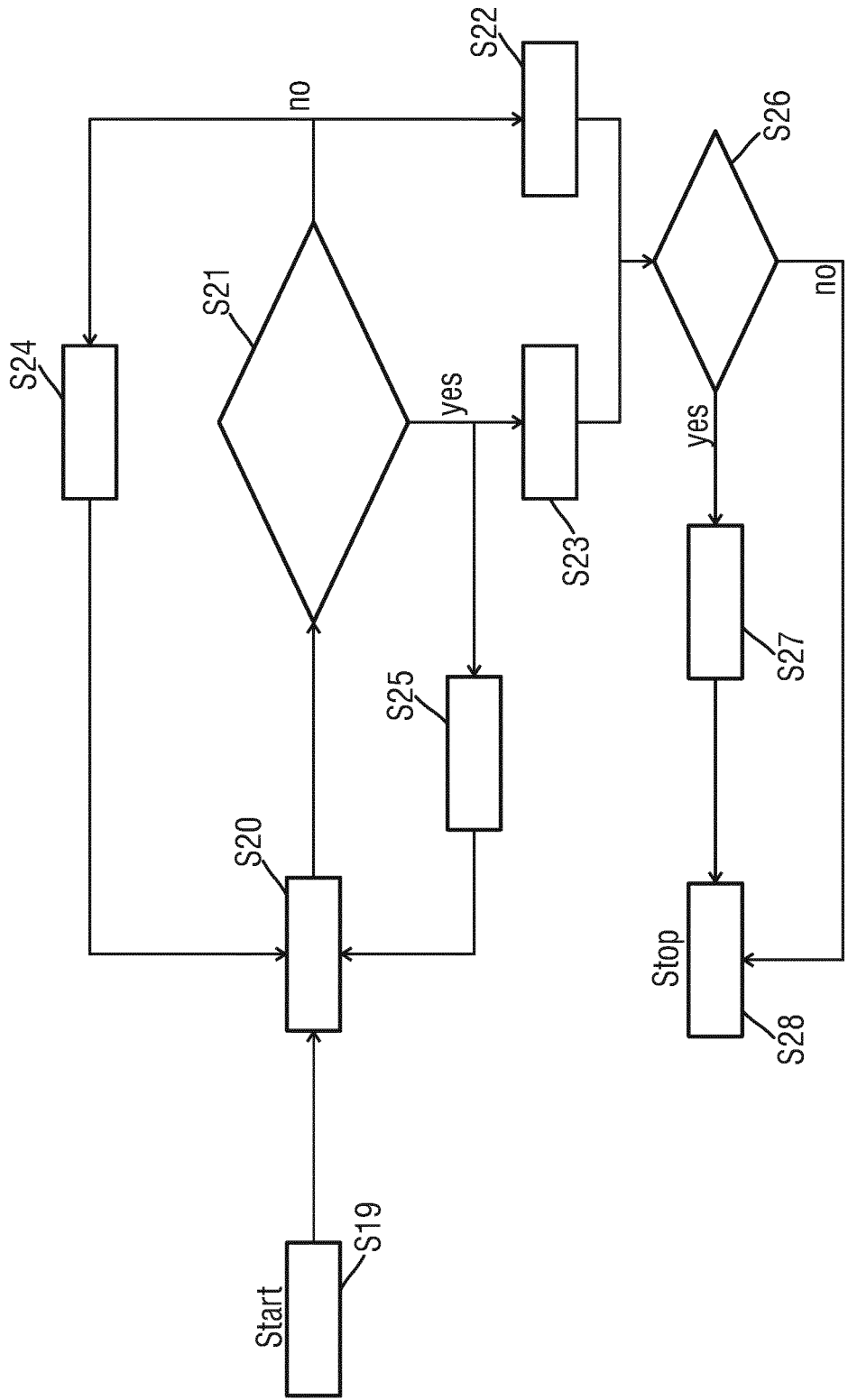
FIG. 8 shows a flow chart of a second part of an embodiment of a method according to the present invention.

FIG. 7 shows a flow chart of a first part of an embodiment of a method according to the present invention, and FIG. 8 shows a flow chart of a second part of an embodiment of a method according to the present invention. In step S10 a measurement of the respiration signal 21 is made, of which a portion S (e.g. of 3.5 min) is treated in the next steps. In steps S11 and S12 a short term activity signal 41a and a long term activity signal 41b are measured, which are used to detect in step S13 if an activity took place in the last X minutes and if a vigorous activity took place in the last X+Y minutes. If this is the case, the method proceeds to step S14, in which the method goes to the next portion S of the respiration signal 21, which is obtained in step S10. Otherwise, the method proceeds to step S15.

In step S15 the portion S is segmented into segments $S_w$, e.g. subsequent windows of 10 s with 5 s overlap. In step S16 it is checked if the segments $S_w$ are stable/not flat, e.g. by checking 25% std (S)<std($S_w$)<75% std(S) (std meaning the standard deviation). Next, in step S17 it is checked if the number of stable/not flat segments $S_w$ is greater than a predetermined number. If this is the case, the respiration signal features for the portion S are calculated in step S18, which are then stored in a features memory in step S19. The method then proceeds to step S14. If the check in step S17 is negative, the method directly proceeds to step S14.

As shown in FIG. 8, starting from the features memory (S19) features are taken at two different times t1, t2 and compared in step S20. In step S21 the features at the second time t2 are different from the features at the first time t1 (with a certain margin). If this is not the case, it is assumed in step S22 that there is no food intake between t1 and t2. If this is the case, it is assumed in step S23 that there is food intake between t1 and t2.

Further, in both cases, in steps S24 and S25 the first and second times t1, t2 are shifted, e.g. by (t2−t1)/2, and the method proceeds with step S20. Further, in both cases, following steps S22 and S23 it is checked in step S26 if there is another equal detection in an adjacent segment S. In the positive case, the adjacent food intake detections are grouped together in step S27, which is then stored in a food intake detections memory in step S28. In the negative case, the food intake detection is directly stored in the food intake detections memory in step S28. This ends the method.

In summary, automatic detection of food ingestion via an unobtrusive method is provide to address the problem of food/drink intake automatic identification via a physiological signal, i.e. respiration, which can be collected unobtrusively. A respiration signal contains a series of features such as dominant frequency and respiration variability derived feature, which are related to the increased oxygen need due to digestion. Respiration data is processed appropriately in order to extract such features. The respiration signal may be filtered to remove motion and other artifacts and unreliable parts of it may be concealed by means of an activity classifier. When respiratory alterations are induced solely by ingestion and physical activity and/or stress can be excluded through use of the classifier, the respiration signal is used to see if from the relevant food/drink intake features such as increased in frequency and/or change in respiratory variability, intake is detected.

The present invention can be used in many fields of application, including weight management programs, undernutrition in patients and undernutrition in elderly people.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for caloric intake detection due to digestion, said device comprising:
   a respiration input for obtaining a respiration signal indicating respiration of a subject,
   an activity input for obtaining activity data indicating physical activity of the subject, and an analysis unit for analyzing the obtained respiration signal and activity data by:
    filtering at least one artefact in the obtained respiration signal to obtain a clean respiration signal, wherein the at least one artefact includes swallowing,
    determining one or more respiration signal features from the obtained clean respiration signal,
    determining the subject is at rest based on the obtained activity data,
    selecting subsequent time windows, wherein the selected subsequent time windows are overlapping time windows, of the obtained clean respiration signal,
    detecting one or more changes of the one or more determined respiration signal feature among the selected subsequent time windows when the subject is at rest, wherein said one or more changes include changes of a group of changes including:
        an increase in respiration frequency,
        an increase of an amplitude of the clean respiration signal,
        a decrease of an inter-breath interval,
        an increase of an amplitude of a dominant frequency in a frequency spectrum of the clean respiration signal, and
        a change in a respiratory variability, and
    detecting a period of caloric intake due to digestion by the subject if one or more of said one or more changes have been detected during said period.

2. The device as claimed in claim 1,
wherein detecting the period of caloric intake due to digestion further includes detecting the period of caloric intake due to digestion by the subject if at least two of said one or more changes have been detected during said period.

3. The device as claimed in claim 1,
wherein said analysis unit is configured to use one or more feature thresholds for detecting changes of the one or more determined respiration signal features.

4. The device as claimed in claim 1,
wherein said analysis unit is configured to select the subsequent time windows for the analysis based on the activity data.

5. The device as claimed in claim 4
wherein said analysis unit is configured to select the subsequent time windows in which the activity data indicate no activity or an activity related to caloric intake or an activity below a predetermined intensity.

6. The device as claimed in claim 4,
wherein said analysis unit is configured to determine duration of the subsequent time windows based on an intensity and duration of a detected activity.

7. The device as claimed in claim 1,
wherein said analysis unit is configured to detect a pre-prandial period and a post-prandial period based on the detected changes of the one or more determined respiration signal features.

8. The device as claimed in claim 7,
wherein said analysis unit is configured to determine an inter-breath interval length as one respiration signal feature and to detect a post-prandial period if the inter-breath interval length decreases.

9. The device as claimed in claim 7,
wherein said analysis unit is configured to determine the dominant frequency as one respiration signal feature and to detect the post-prandial period if the dominant frequency increases.

10. A system for caloric intake detection, said system comprising:
    a respiration sensor for detecting the subject's respiration and for generating the respiration signal indicating the subject's respiration, and
    the device as defined in claim 1 for caloric intake detection based on the generated respiration signal.

11. The system as claimed in claim 10,
wherein said respiration sensor comprises a wearable sensor, and wherein the wearable senor is one of a respiration belt, a wrist worn sensor, an ECG sensor, a contact photoplethysmography sensor, a remote sensor, a remote photoplethysmography sensor or a camera.

12. The system as claimed in claim 10,
further comprising an activity sensor, wherein the activity sensor is one of an accelerometer or a remote camera, for acquiring activity data indicating the physical activity of the subject, wherein said analysis unit is configured to use the acquired activity data in detecting caloric intake of the subject in determining the subject is at rest.

13. A method for use by a computer, processor or device for automatic caloric intake detection due to digestion, said method comprising:
    obtaining a respiration signal indicating respiration of a subject,
    obtaining activity data indicating physical activity of the subject,
    analyzing the obtained respiration signal and activity data by:
        filtering at least one artefact in the obtained respiration signal to obtain a clean respiration signal, wherein the at least one artefact includes swallowing,
        determining one or more respiration signal features from the obtained clean respiration signal,
        determining the subject is at rest based on the obtained activity data,
        selecting subsequent time windows, wherein the selected subsequent time windows are overlapping time windows, of the obtained clean respiration signal,
        detecting one or more changes of the one or more determined respiration signal features among the selected subsequent time windows when the subject is at rest, wherein said one or more changes include changes of a group of changes including:
            an increase in respiration frequency,
            an increase of an amplitude of the clean respiration signal,
            a decrease of an inter-breath interval,
            an increase of an amplitude of a dominant frequency in a frequency spectrum of the clean respiration signal, and
            a change in a respiratory variability, and
        detecting a period of caloric intake due to digestion by the subject from the detected one or more of said one or more changes during said period.

14. A non-transitory computer-readable storage medium, having stored thereon a computer program comprising program code which, when executed by the processor performs the method as claimed in claim 13.

\* \* \* \* \*